United States Patent [19]

Hacke et al.

[11] 4,399,127

[45] Aug. 16, 1983

[54] INJECTABLE OXYTETRACYCLINE COMPOSITIONS

[75] Inventors: Walter Hacke, Rutherford, N.J.; Herman Horn, Staten Island, N.Y.

[73] Assignee: Diamond Shamrock Corporation, Dallas, Tex.

[21] Appl. No.: 300,007

[22] Filed: Sep. 8, 1981

Related U.S. Application Data

[63] Continuation of Ser. No. 139,147, Apr. 10, 1980, abandoned.

[51] Int. Cl.$^3$ ............................................. A61K 31/65
[52] U.S. Cl. ................................................... 424/227
[58] Field of Search ......................................... 424/227

[56] References Cited

U.S. PATENT DOCUMENTS

| | | | |
|---|---|---|---|
| 3,557,280 | 1/1971 | Weber et al. | 424/80 |
| 3,712,949 | 1/1973 | Greenbaum et al. | 424/227 |
| 3,957,972 | 5/1976 | Weber et al. | 424/80 |
| 4,018,889 | 4/1977 | Armstrong | 424/80 |
| 4,126,680 | 11/1978 | Armstrong | 424/80 |

*Primary Examiner*—Stanley J. Friedman
*Attorney, Agent, or Firm*—Neal T. Levin

[57] ABSTRACT

Increased antibiotic content of oxytetracycline injectable compositions containing glycerol formal as the solvent is achieved by utilization of particular magnesium compounds, viz., magnesium oxide, magnesium hydroxide, magnesium carbonate, magnesium acetate and magnesium chloride. Magnesium chloride is utilized with oxytetracycline base only.

9 Claims, No Drawings

INJECTABLE OXYTETRACYCLINE COMPOSITIONS

This is a continuation of application Ser. No. 139,147, filed Apr. 10, 1980, now abandoned.

BACKGROUND OF THE INVENTION

1. Field of the Invention

This invention relates to oxytetracycline injectable compositions having increased antibiotic content.

2. Description of the Prior Art

Heretofore, preparations of oxytetracycline compositions suitable for injection have suffered from relatively high viscosities, poor stability and limited concentration of antibiotic. Such preparations have employed solvents such as propylene glycol, glycerol and polyethylene glycols as well as their mixtures with ethanol. High viscosities are particularly noticeable when injectable compositions containing polyhydric alcohols as solvents are used at low temperatures. Such high viscosities are often encountered when the compositions are used at the cool temperatures prevailing in barns, open feedlots or pastures. High viscosity compositions are objectionable because aspiration of a viscous composition into a hypodermic syringe and subsequent injection of the composition are both difficult and slow. Further, high viscosities also increase the time required to inject a large herd of animals. Other solvents may cause tissue irritation which is particularly undesirable in an animal as they may cause localized concentration of the antibiotic in the tissue and render the affected area undesirable for human consumption.

It is known according to U.S. Pat. No. 3,712,949—Greenbaum et al.—Jan. 23, 1973, to prepare injectable oxytetracycline solutions utilizing glycerol formal as the solvent, a water soluble magnesium salt such as magnesium chloride hexahydrate, antioxidant, buffering agent and water. These compositions overcome the disadvantages specified above, i.e., they are characterized as having lower viscosities at low temperatures and having excellent stability as to color, antibiotic potency and physical state. However, the maximum antibiotic concentration which has been achieved is approximately 15% by weight of the total composition. It is desirable to prepare compositions having greater antibiotic concentration. This is of great importance because a composition having a greater antibiotic concentration permits reduction of the number of injections at any one time in large animals such as cattle. In the case of a large herd, this reduces both time and labor. Additionally, a reduced number of injection sites in an animal brings about less damage to the quality of the meat.

SUMMARY OF THE INVENTION

Oxytetracycline injectable compositions having increased antibiotic concentrations where glycerol formal is the solvent have been achieved by employing particular magnesium compounds, viz., magnesium oxide, magnesium hydroxide, magnesium carbonate, magnesium acetate and with oxytetracycline base only, magnesium chloride. These compositions can contain from, e.g., about 15% by weight to about 35% by weight oxytetracycline. These compositions permit a reduction in the number of injections at any one time in large animals. Further, they are characterized by their stability and low viscosities at low temperatures. Thus, fluid oxytetracycline compositions of enhanced antibiotic content suitable for injection over a wide range of temperatures, including low temperatures are provided for. Excellent stability of color, potency and physical state is achieved. Further, animals injected with these compositions are free of irritation at the site of the injection.

DESCRIPTION OF THE PREFERRED EMBODIMENTS

The relative proportions of the constituents can be varied widely. For example, the quantity of antibiotic such as oxytetracycline base or an acid addition salt thereof can vary from about 15.0 to about 35.0 parts by weight.

The mole ratio of magnesium compound such as magnesium oxide to oxytetracycline base or acid addition salt can be varied from about 0.8 to about 1.2 moles of magnesium compound per mole of antibiotic. Preferably the mole ratio of magnesium compound to oxytetracycline base is about 1:1 while the mole ratio of magnesium compound to oxytetracycline hydrochloride is about 0.8 to 1. Lower ratios tend to give deeper color on standing while higher ratios tend to give both deeper color and cause precipitation on standing. With higher quantities of antibiotic, the quantity of magnesium compound should be maintained near its lower range, i.e., the mole ratio of magnesium compound to antibiotic should be about 0.8 to 1 to avoid higher concentrations of magnesium compound which may adversely affect the viscosity.

The quantity of glycerol formal can vary from about 50 to about 95 parts by weight, the upper limit being regulated, of course, by the quantities of the other constituents.

The quantity of water can be varied from about 10 to as much as about 45 parts by weight. Above 45 parts by weight of water, a turbid composition is formed. The presence of water is desirable to assist solution of the inorganics and to obtain an injectable composition which causes no visible tissue damage. Ethyl alcohol up to about 20 parts by weight can be substituted for part of the water or part of the glycerol formal in the composition to obtain a composition having even a lower viscosity.

An effective amount of an antioxidant is added. Sufficient buffering agent is added to provide a composition having a pH of from about 6 to about 9.5.

Glycerol formal, a condensation product of glycerol and formaldehyde is obtained as a mixture of 4-hydroxymethyl-1,3-dioxolane and 5-hydroxy-1,3-dioxane. The mixture obtained as the product of the reaction, or a mixture made by fortifying the product of the reaction with one of the components, or the individual components can be used in the present invention.

With respect to the magnesium compound, magnesium oxide, magnesium hydroxide, magnesium carbonate and magnesium acetate can be used. With oxytetracycline base only, magnesium chloride can be used. Magnesium oxide is preferred.

Antioxidants are used in addition to manufacturing and storing the compositions of this invention in an inert atmosphere. The antioxidants assist in the stabilization of the color and potency of the compositions. Any antioxidant which is physiologically acceptable for use in a parenteral drug composition and which is compatible with oxytetracycline can be used in the present invention. Suitable antioxidants include sodium bisulfite, sodium metabisulfite, sodium formaldehydesulfoxylate and monothioglycerine. Generally from about 0.05 to about 5 parts by weight, preferably about 0.5 to about 2 parts by weight of antioxidant are used.

An inert atmosphere such as nitrogen, helium or the like is not necessary for maintenance of potency, but aids considerably in the retention of a light colored composition on long storage.

The compositions of the present invention are prepared by mixing an oxytetracycline antibiotic, in its free base form (oxytetracycline base) or as an acid addition salt, with the magnesium compound in water or the glycerol formal solvent. When water is employed, the glycerol formal solvent is then added to the aqueous solution in appropriate quantity.

The pH of the composition is then adjusted to about 6.0 to about 9.5 with a buffering agent, e.g., physiologically acceptable bases such as sodium hydroxide, potassium carbonate, ammonia or physiologically acceptable lower aliphatic primary, secondary and tertiary amines having up to about six carbon atoms per group attached to the amino nitrogen atom. These amines include ethanolamine (2-aminoethanol), diethylamine, ethylamine, triethanolamine, diethanolamine, arginine, glucosamine or the like. The final pH of the composition is ordinarily not critical, however, best stability appears to reside with moderate pH value, i.e., between about 6.0 to about 9.5. Lower pH values cause too rapid decomposition of the antioxidant while too high a pH increases color formation. Also when the final pH is above about 9.5, physiological compatibility of the composition with the muscle tissue is decreased. A final pH slightly on the alkaline side is preferred in order to minimize local tissue irritation on parenteral administration. The most satisfactory range is from about 6.0 to about 9.5, preferably from about 7.5 to about 8.5.

For injection, the finished composition must be sterile. That is, sterile components and sterile conditions of manufacture must be employed, or alternatively, the composition itself must be sterilized after manufacture such as by sterile filtration.

Regarding the selection of the antibiotic, oxytetracycline free base or an acid addition salt of same such as oxytetracycline hydrochloride, oxytetracycline phosphate, oxytetracycline sulfate, oxytetracycline acetate or the like can be used. Where a light colored final product is desired, a light colored antibiotic should be used.

For a fuller understanding of this invention, reference may be made to the following examples. These examples are merely to illustrate the invention and are not to be construed in a limiting sense.

In the following examples, the glycerol formal contained 50% by weight of 4-hydroxymethyl-1,3-dioxolane and 50% by weight of 5-hydroxy-1,3-dioxane. This material can be prepared as described in Example I of U.S. Pat. No. 3,712,949.

The oxytetracycline assay procedure utilized is described in 21 Code of Federal Regulations Part 446.265, page 541 and Part 446.267, page 542, Apr. 1, 1978 revision. See portions entitled Oxytetracycline injectable and references referred to therein.

EXAMPLE I

This example describes the preparation and stability of a 20% by weight oxytetracycline solution using glycerol formal as the solvent and a water soluble magnesium salt.

Under nitrogen atmosphere, 57.5 grams oxytetracycline hydrochloride having a potency of 890 mcg/mg were dissolved in a solution of 30 ml distilled water and 48 grams of glycerol formal. The resulting mixture was stirred until dispersed. Then 18.0 grams of reagent grade magnesium chloride hexahydrate was added. The mole ratio of magnesium to oxytetracycline was 0.8 to 1. Additional glycerol formal was added so that the total amount of glycerol formal used was 195 grams. The resulting mixture was warmed to 40° C. and stirred until a clear solution was obtained (about 1¼ hrs.). The resulting solution was cooled to about 20°-25° C. and sufficient monoethanolamine was added over about 1 hour to adjust the pH to 8.3-8.4. Then a solution of 2.5 grams of sodium formaldehyde sulfoxylate in 6 ml water was slowly added (a slight yellow precipitate formed which dissolved after a few minutes) and the resulting solution stirred until a constant pH of 8.3-8.4 was attained. Additional monoethanolamine was added to maintain the pH. About 2 hours were required during which time a total of 23.1 ml of monoethanolamine was added. The potency of the resulting solution was 210 mg oxytetracycline/ml. Its viscosity was 140 centipoise at 5° C. and 90 centipoise at 21° C. This solution was filtered through a 0.2 micron membrane filter.

Stability studies were conducted. Samples on storage at 45° C. were stable only for 29 to 39 days while samples on storage at 37° C. were stable only for 137 to 153 days. Formation of a yellow precipitate was taken as evidence of instability.

EXAMPLE II

This example describes the preparation and stability of a 20% by weight oxytetracycline base solution.

Under nitrogen atmosphere, 2.0 grams of sodium formaldehyde sulfoxylate were dissolved in 50 ml distilled water. Then 3.8 grams magnesium oxide were added, the mixture stirred and 46 grams oxytetracycline base having a potency of 920 mcg/mg and 144 grams glycerol formal were added. The mole ratio of magnesium to oxytetracycline was 1 to 1. The resulting mixture was heated at 40° C. for 20 minutes until a practically clear solution was obtained. It was cooled to 20° C. and the pH adjusted to 8.4 with 1.4 ml monoethanolamine. About 2 hours was required for pH stabilization. The solution had a potency of 206 mg oxytetracycline/ml. The solution containing 20.6% by weight oxytetracycline was filtered through a 0.2 micron membrane filter.

Samples were stored at 37° C. for over 200 days. No yellow precipitation was observed.

Additional preparations containing oxytetracycline base tabulated below, were prepared in a manner similar to the preparation of the composition of Example II.

| Example No. | PARTS BY WEIGHT | | | |
| --- | --- | --- | --- | --- |
| | III | IV | V | VI |
| Ingredients: | | | | |
| Oxytetracycline base (potency:920 mcg/mg) | 22.4 | 48.0 | 48.0 | 48.0 |
| Magnesium oxide | 1.9 | 4.0 | 4.0 | 4.6 |
| 2-aminoethanol | 0.8 | 1.1 | 1.0 | 0 |
| Sodium formaldehyde sulfoxylate | 1.0 | 2.1 | 2.0 | 2.0 |
| Glycerol formal | 72.0 | 144.0 | 130.0 | 130.0 |
| Water | 20.0 | 60.0 | 72.0 | 72.0 |
| % Oxytetracycline | 20.2 | 19.5 | 20.3 | 20.4 |
| Mole ratio of magnesium to oxytetracycline | 1.1 to 1 | 1 to 1 | 1 to 1 | 1.2 to 1 |

EXAMPLE VII

This Example describes the preparation of a 20% by weight oxytetracycline solution prepared from oxytetracycline base.

A 2 liter glass vessel was evacuated and flushed with nitrogen. Then 576 ml of distilled water was added, the vessel stirred and 9.6 grams of sodium formaldehyde sulfoxylate added. Eight minutes were required to dissolve the antioxidant. Glycerol formal, 814 ml, was added. Magnesium oxide 30.5 grams and oxytetracycline base of 91% purity, 384 grams, were added. The antibiotic was rinsed in with an additional 50 ml of glycerol formal. Approximately 20 minutes was required for addition of magnesium oxide and oxytetracycline; seven minutes for dissolving the reactants. During addition of the oxytetracycline the temperature rose to 36° C. Occasional heating to dissolve the oxytetracycline was required. Stirring was continued for one-half hour, the temperature at 30° C. The pH was 7.4. Monoethanolamine, 11.8 ml, was added dropwise during the course of eight minutes with stirring. The pH, after addition, was 8.2. Stirring was continued and the system allowed to equilibrate for two hours during which an additional 1.6 ml of monoethanolamine were added. Final pH was 8.2; final volume was 1,700 ml.

The solution was pre-filtered through No. 3 Whatman filter paper. The solution was then filtered through a 0.2 micron membrane filter (Millipore Corporation, Bedford, Mass.).

The solution had the following characteristics:

| | |
|---|---|
| Antibiotic potency (calculated) | 206 mg/ml |
| Antibiotic potency (by duplicate assay) | 200, 194 mg/ml |
| Specific gravity | 1.192 |
| Viscosity | 19.3 cps at 24° C.; 22.1 cps at 22° C. and 50 cps at 0° C. |
| Mole ratio of magnesium to antibiotic | 1 to 1 |

Stability studies were conducted both at ambient temperature and at 37° C. with the data reported below. Assay data is the average of two determinations.

| Time (Months) | Initial | 3 | 6 | 9 | 12 |
|---|---|---|---|---|---|
| AMBIENT TEMPERATURE | | | | | |
| Antibiotic potency (mg/ml) | 197 | 208 | 201 | 207 | 207 |
| Color | Amber | Amber | Amber | Amber | Dark Amber |
| pH | 8.2 | 8.1 | 8.1 | 8.2 | 8.3 |
| AT 37° C. | | | | | |
| Antibiotic potency (mg/ml) | 197 | 208 | 197 | 196 | 203 |
| Color | Amber | Amber | Dark Amber | Dark Amber | Dark Amber |
| pH | 8.2 | 8.2 | 8.2 | 8.3 | 8.4 |

EXAMPLE VIII

This Example describes the preparation of a 20% by weight oxytetracycline solution prepared from oxytetracycline hydrochloride.

A 2 liter glass vessel was evacuated and flushed with nitrogen. Then 300 ml of water and 23 grams of magnesium oxide were added with stirring to disperse the magnesium oxide. Glycerol formal, 800 ml and oxytetracycline hydrochloride of 91% oxytetracycline purity, 360 grams, were added with stirring to dissolve the antibiotic. Antibiotic addition required ten minutes during which time, the temperature rose to 41° C. Glycerol formal, 130 ml, was added to rinse in the antibiotic followed by stirring for one hour. The temperature was 32° C. and pH was 3.8. Monoethanolamine, 80 ml was added over 40 minutes. The temperature was 32° C. and pH rose to 8.2. A sodium formaldehyde sulfoxylate solution, 8 grams dissolved in 20 ml of water, was added. A precipitate was formed which dissolved within five minutes. Stirring was carried out one and one-half hours to allow for pH equilibrium. The pH was then adjusted to 8.2–8.4 with additional monoethanolamine. Final volume of the solution was 1,510 ml.

The solution was filtered through a 0.2 micron membrane filter.

The solution had the following characteristics:

| | |
|---|---|
| Antibiotic potency (calculated) | 206 mg/ml |
| Antibiotic potency (by duplicate assay) | 193, 202 mg/ml |
| Specific gravity | 1.233 |
| Viscosity | 47.3 cps at 23° C. |
| Mole ratio of magnesium to antibiotic | 0.8 to 1 |

Stability studies were conducted both at ambient temperature and at 37° C. with the data reported below. Assay data is the average of two determinations.

| Time (Months) | Initial | 3 | 6 | 9 | 12 |
|---|---|---|---|---|---|
| AMBIENT TEMPERATURE | | | | | |
| Antibiotic potency (mg/ml) | 198 | 212 | 212 | 206 | 206 |
| Color | Light Amber | Light Amber | Light Amber | Light Amber | Amber |
| pH | 8.6 | 8.5 | 8.3 | 8.5 | 8.7 |
| AT 37° C. | | | | | |
| Antibiotic potency (mg/ml) | 198 | 215 | 189 | 203 | 206 |
| Color | Light Amber | Light Amber | Light Amber | Light Amber | Dark Amber |
| pH | 8.6 | 8.6 | 8.3 | 8.5 | 8.7 |

The following oxytetracycline solutions were prepared from oxytetracycline base using the procedure of Example VII.

| Example No. | IX | X | XI | XII | XIII | XIV |
|---|---|---|---|---|---|---|
| Ingredients: | | | | | | |
| Distilled water (ml) | 90 | 48 | 70 | 66 | 38 | 70 |
| Glycerol formal (ml) | 90 | 72 | 105 | 100 | 38 | 105 |
| Magnesium acetate tetrahydrate (grams) | — | — | — | — | — | 19.4 |
| Magnesium oxide (grams) | 4.0 | — | — | 4.75 | 2.7 | — |
| Basic magnesium carbonate (grams) | — | 11 | — | — | — | — |
| Magnesium hydroxide (grams) | — | — | 5.7 | — | — | — |
| Oxytetracycline base potency 920 mcg/mg (grams) | 48 | 37 | 48 | 60.0* | 34 | 49* |
| Sodium formaldehyde sulfoxylate (grams) | 2.1 | 1.9 | 2.0 | 1.2 | 1.0 | 1.1 |
| Monoethanolamine (ml) | — | 1.0 | 2.0 | 1.5 | 1.0 | 13.25 |
| pH | 8.5 | 8.3 | 8.4 | 8.5 | 8.4 | 8.3 |

-continued

| Example No. | IX | X | XI | XII | XIII | XIV |
|---|---|---|---|---|---|---|
| Antibiotic potency by assay (mg/ml) | 202 | 198 | 200 | 250–260 | 318 | 203 |
| Mole ratio of magnesium to antibiotic | 1 to 1 | 1.2 to 1 | 1 to 1 | 1 to 1 | 1 to 1 | 1 to 1 |
| % by wt. of antibiotic | 20 | 20 | 20 | 25 | 32 | 20 |

*Oxytetracycline potency was 912/mcg/mg

EXAMPLE XV

This Example describes tests conducted in pigs to evaluate blood levels of antibiotic, local reaction at the site of injection and tissue residues of antibiotic.

Two formulas were utilized, each containing approximately 200 mg oxytetracycline/ml (approximately 20% by weight oxytetracycline). The composition of each formula is set forth below.

| Formula No. | A | B |
|---|---|---|
| Ingredients: | | |
| Distilled water (ml) | 150 | 192 |
| Glycerol formal (ml) | 450 | 288 |
| Magnesium oxide (grams) | 11.5 | 10.2 |
| Oxytetracycline hydrochloride, potency 910 mcg/mg (grams) | 180 | — |
| Oxytetracycline base, potency 910 mcg/mg (grams) | — | 128 |
| Monoethanolamine (ml) | 37.8 | 4.45 |
| Sodium formaldehyde sulfoxylate (grams) | 4.5 | 3.2 |
| pH | 8.2 | 8.2 |
| Antibiotic potency by assay (mg/ml) | 202 | 203 |
| Mole ratio of magnesium to antibiotic | 0.85 to 1 | 1.1 to 1 |
| % by wt. antibiotic | 20 | 20 |

Eight healthy pigs about three months old, were ear tagged with numbers at the time of purchase. These pigs weighing 21.8–30.9 kg were kept in a 16′×28′ covered concrete floor pen bedded with wood shavings. All pigs were fed antibiotic free grower ration containing 15% of protein. Water was supplied free choice.

The experimental design is shown in Table I below.

TABLE I

| Formula | No. of Pigs | Dose of Injectable Intramuscular | Serum Sampling Post Injection | Slaughter Day Post Injection |
|---|---|---|---|---|
| Control | 2 | Control (no injection given) | 0,2,4,8,12, and 24 hours post injection and every 24 hours for next 6 days | One pig each on day 20 and 30 |
| A | 3 | 1 ml/10 kg of body weight (20 mg of OTC/ kg of body weight) | 0,2,4,8,12, and 24 hours post injection and every 24 hours for next 6 days | One pig each on day 25 and 30 |
| B | 3 | 1 ml/10 kg of body weight (20 mg of OTC/ kg of body weight) | 0,2,4,8,12, and 24 hours post injection and every 24 hours for next 6 days | One pig each on day 25 and 30 |

The pigs weighed 28.1–30.9/kg after 20 days of acclimation period. Blood samples were collected from all pigs before injection. The two control pigs were not injected with an oxytetracycline formulation. The respective formulations of oxytetracycline were injected intramuscularly at doses of 20 mg of oxytetracycline per kg body weight. Blood samples were collected from all pigs at 2, 4, 8, 12 and 24 hours post injection and at every 24 hours during next 6 days. Clear serum was collected from all blood samples and kept frozen. Oxytetracycline assays were conducted by method recognized by Food and Drug Administration. See Kramer, J., et al., "Antibiotic Residues in Milk, Dairy Products, and Animal Tissues: Methods, Reports, and Protocols". National Center for Antibiotic Analysis, Food and Drug Administration, Washington, D.C. 1968. One pig administered Formula A died soon after 8 hour bleeding because of a rip in the vena cava. The average value of oxytetracycline serum level for each injection group is set forth in Table II below.

TABLE II

AVERAGE OXYTETRACYCLINE SERUM LEVELS AFTER INTRAMUSCULAR INJECTION OF OXYTETRACYCLINE 20% FORMULATIONS IN PIGS

| Oxytetracycline Injectable Formula | Hours post injection/mg of Oxytetracycline/gram of Serum | | | | | | | | | | | |
|---|---|---|---|---|---|---|---|---|---|---|---|---|
| | 0 | 2 | 4 | 8 | 12 | 24 | 48 | 72 | 96 | 120 | 144 | 168 |
| A | <0.07 | 2.25 | 2.73 | 2.35 | 1.94 | 1.13 | 0.41 | 0.22 | 0.16 | 0.08 | 0.07 | 0.07 |
| B | <0.08 | 4.05 | 3.74 | 3.11 | 2.69 | 1.47 | 0.41 | 0.26 | 0.21 | 0.10 | <0.08 | <0.08 |
| Control | <0.04 | <0.04 | <0.04 | <0.04 | <0.04 | <0.04 | <0.04 | <0.04 | <0.04 | <0.04 | <0.04 | <0.04 |

Results indicate that Formula B gave sustained higher serum levels of oxytetracycline up to 5 days post injection when compared to the data on Formula A.

All injection sites were examined for redness, swelling, hardness, abscess, sloughing or any other local reaction before the animals were sacrificed. No unusual local reaction was observed at the injection sites. All injection sites were incised after sacrifice of the pigs. None of the injection sites showed reaction to be a problem in clinical use of these formulations.

Muscle from the injection sites, samples of liver, kidney, fat and muscle from non-injected area were assayed for oxytetracycline residues using FDA recognized method. See Kramer, J., et al., "Antibiotic Residues in Milk, Dairy Products, and Animal Tissue: Methods, Reports and Protocols". National Center for Antibiotic Analysis, Food and Drug Administration, Washington, D.C. 1968. The results of tissue assays are reported in Table III below.

TABLE III

TISSUE RESIDUES OF OXYTETRACYCLINE AFTER INTRAMUSCULAR INJECTION OF 20% OXYTETRACYCLINE INJECTABLES AT A DOSE OF 20 MG/KG BODY WEIGHT

| Formula | No. of Pigs Slaughtered on Day Post Injection | | | Tissue Residues of Oxytetracycline mg/g | | | | Injection Site |
|---|---|---|---|---|---|---|---|---|
| | 20 | 25 | 30 | Muscle | Kidney | Liver | Fat | |
| A | 1 | | | <0.02 | 0.22 | 0.94 | 0.12 | 0.14 |
| | | 1 | | 0.04 | 0.16 | <0.06 | 0.10 | 0.08 |
| B | 1 | | | 0.39 | 0.18 | <0.06 | 0.04 | <0.06 |
| | | 1 | | 0.14 | 0.17 | <0.06 | <0.04 | <0.06 |
| | | | 1 | <0.02 | 0.17 | <0.06 | <0.04 | <0.06 |

The data indicates that pigs sacrificed on day 20, 25, and 30 post injection with Formula B showed comparatively lower residues than pigs injected with Formula A on corresponding days.

EXAMPLE XVI

This Example describes the preparation of a 20% by weight oxytetracycline solution prepared from oxytetracycline hydrochloride.

Distilled water (38 ml), 13.3 grams magnesium acetate tetrahydrate, 45 grams oxytetracycline hydrochloride having a potency of 910 mcg/mg and 115 ml glycerol formal were stirred under nitrogen atmosphere at 30°–40° C. for about one hour. The clear solution was allowed to cool to ambient temperature, the pH adjusted to about 8–8.2 with 15 ml monoethanolamine and 1.0 gram sodium formaldehyde sulfoxylate then added. After about one hour, the sodium formaldehyde sulfoxylate had dissolved and stirring was continued for about two hours to a constant pH of 8.3, during which time monoethanolamine was added as required. The total volume used was 16.6 ml. The volume of oxytetracycline solution was 205 ml and it assayed 208 mg/ml oxytetracycline (duplicate assays). The mole ratio of magnesium to antibiotic was 0.8 to 1. After 30 days of storage at 45° C., at 37° C. and at room temperature, no oxytetracycline precipitate was observed.

EXAMPLE XVII

This Example describes the preparation of a 20% by weight oxytetracycline solution prepared from oxytetracycline base.

The procedure was the same as Example VIII, but using the following:

| Ingredients | Quantity |
|---|---|
| Distilled water | 38 ml |
| Magnesium chloride hexahydrate | 16.8 grams |
| Oxytetracycline (potency: 905 mcg/mg) | 45 grams |
| Glycerol formal | 115 ml |
| Monoethanolamine | 13.2 ml |
| Sodium formaldehyde sulfoxylate | 1.0 gram |

The volume of antibiotic solution was 200 ml. Final pH was 8.25 and assayed 200 mg/ml oxytetracycline (duplicate assays). Mole ratio of magnesium to antibiotic was 1 to 1.

After 30 days of storage at 45° C. and 37° C. no oxytetracycline precipitate was observed. At room temperature, no oxytetra- precipitate was observed even after two months.

While the invention has been described with reference to certain specific embodiments thereof, it is understood that it is not to be so limited since alterations and changes may be made therein which are within the full intended scope of the appended claims.

What is claimed is:

1. A stable, injectable antibiotic composition of increased antibiotic concentration for parenteral administration comprising:
   (a) from about 15 to about 35 parts by weight of an antibiotic selected from the group consisting of oxytetracycline base and an acid addition salt thereof,
   (b) a magnesium compound selected from the group consisting of magnesium oxide, magnesium hydroxide and magnesium carbonate present in a molar ratio from about 0.8 to about 1.2 moles per mole of said antibiotic,
   (c) from about 50 to about 95 parts by weight of glycerol formal selected from the group consisting of 4-hydroxymethyl-1,3-dioxolane, 5-hydroxy-1,3-dioxane and mixtures thereof,
   (d) from about 10 to about 45 parts by weight of water,
   (e) an antioxidant in an amount sufficient to stabilize said composition, and
   (f) a buffering agent in an amount sufficient to provide a pH of from about 6 to about 9.5 in said composition.

2. The composition of claim 1 wherein said antibiotic is oxytetracycline base, said magnesium compound is magnesium oxide and said glycerol formal is a mixture of 4-hydroxymethyl-1,3-dioxolane and 5-hydroxy-1,3-dioxane.

3. The composition of claim 1 wherein said antibiotic is oxytetracycline hydrochloride, said magnesium compound is magnesium oxide and said glycerol formal is a mixture of 4-hydroxymethyl-1,3-dioxolane and 5-hydroxy-1,3-dioxane.

4. The composition of claim 2 wherein the mole ratio of said magnesium compound to said oxytetracycline base is about 1 to 1.

5. The composition of claim 4 wherein the amount of oxytetracycline base present is about 20 % by weight of the total composition.

6. The composition of claim 3 wherein the mole ratio of said magnesium compound to said oxytetracycline hydrochloride is 0.8 to 1.

7. The composition of claim 1 wherein said antioxidant is sodium formaldehydesulfoxylate.

8. The composition of claim 1 wherein said buffering agent is monoethanolamine.

9. The composition of claim 1 wherein substantially all particles thereof are smaller than 0.20 microns.

* * * * *